United States Patent [19]

Jalalian

[11] Patent Number: 5,158,098

[45] Date of Patent: Oct. 27, 1992

[54] PELVIC BELT WITH HAND MOUNTS FOR SPINAL UNLOADING

[76] Inventor: Armen Jalalian, 76 Hernandez Ave., San Francisco, Calif. 94127

[21] Appl. No.: 821,278

[22] Filed: Jan. 10, 1992

Related U.S. Application Data

[63] Continuation of Ser. No. 588,443, Sep. 26, 1990, abandoned.

[51] Int. Cl.⁵ ............................................... A61F 5/37
[52] U.S. Cl. ...................................... 128/876; 128/845
[58] Field of Search ............... 128/845, 846, 875, 876, 128/102.1, 101.1, 100.1, DIG. 20

[56] References Cited

U.S. PATENT DOCUMENTS

| 1,722,205 | 7/1929 | Freund | 2/44 |
|---|---|---|---|
| 2,250,267 | 7/1941 | Lins | 128/845 |
| 3,029,810 | 4/1962 | Martin | 602/19 |
| 3,888,245 | 6/1975 | Berntson et al. | 128/78 |
| 4,022,197 | 5/1977 | Castiglia | 128/101.1 |
| 4,172,453 | 10/1979 | Leckie | 128/876 X |
| 4,572,167 | 2/1986 | Brunswick | 602/19 |
| 4,860,560 | 8/1989 | Lundelius | 128/876 X |
| 5,062,414 | 11/1991 | Grim | 128/DIG. 20 |
| 5,065,773 | 11/1991 | Jackson et al. | 128/876 |

Primary Examiner—Robert A. Hafer
Assistant Examiner—Brian E. Hanlon
Attorney, Agent, or Firm—Flehr, Hohbach, Test, Albritton & Herbert

[57] ABSTRACT

An orthotic pelvic belt (10) having a pair grips (B) on the rear of a waistband (A). The waistband may also have a back support section (2) and a pair of straps (1a, 1b) on either side of the back support section (2). The straps (1a, 1b) may be joined together by a belt buckle (4). The hand grips (B) have a plurality of rivets (6) which are inserted into corresponding rivet holes (3) on the waistband (A).

30 Claims, 1 Drawing Sheet

FIG. 2
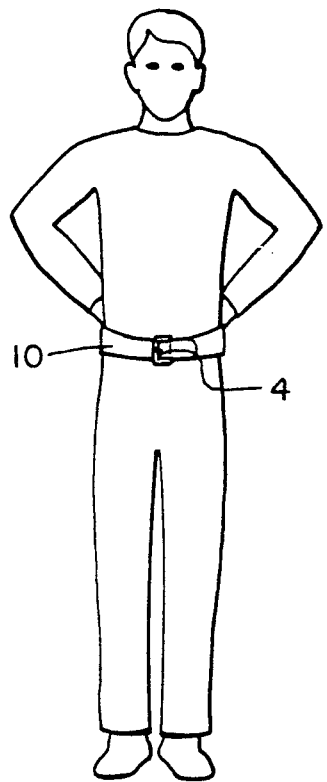
FIG. 3
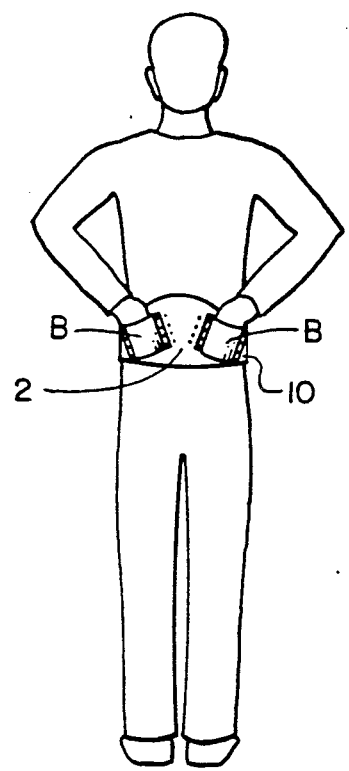
FIG. 4
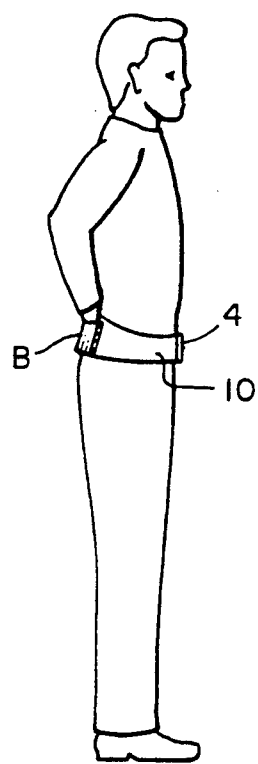
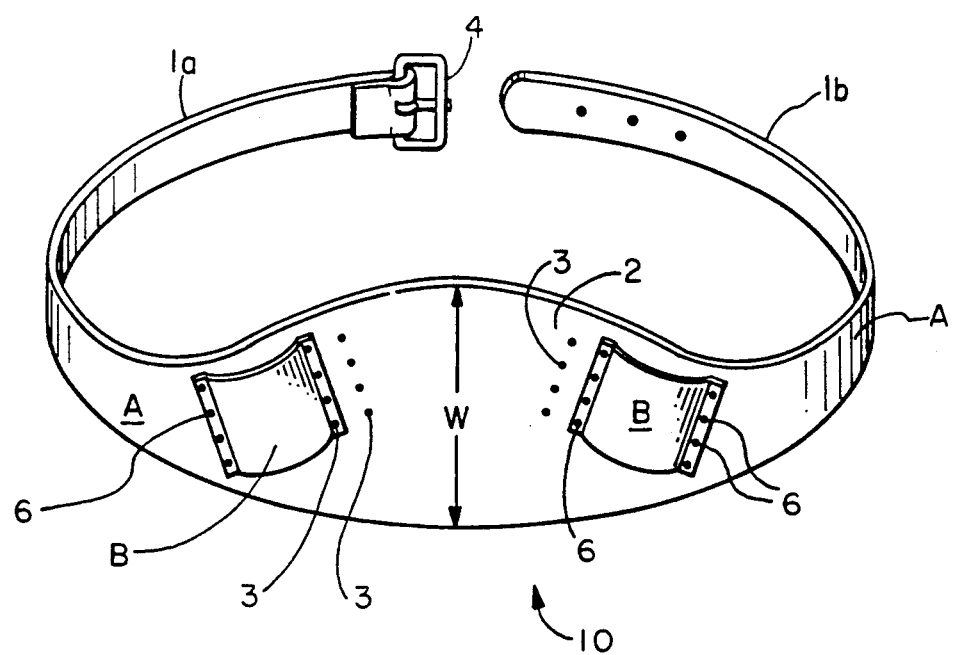
FIG. 1

PELVIC BELT WITH HAND MOUNTS FOR SPINAL UNLOADING

This is a continuation of application Ser. No. 07/588,443 filed Sep. 26, 1990 abandoned.

BACKGROUND

1. Field of the Invention

The present invention broadly relates to a orthotic belt and more particularly to a pelvic belt with hand grips for transferring upper body compression forces off the spinal column and onto the pelvic bones.

2. Background Art

The spinal column of the human body is notoriously susceptible to disability; 80% of the population experiences back pain during their lifetime. The mechanism of back injury is not clearly understood; however, it is generally accepted that mechanical factors play a significant role in the onset of back pain. The spinal column vertebrae and intervertebral discs represent the static and dynamic compressive members which support the mechanical forces of the upper body, head and arms.

Disability caused by injury, surgery and cumulative fatigue adversely affect the spinal column's ability to support the static and dynamic compressive loads of an injured individual's upper torso. Examples of such disability are disc herniation, disk degeneration with age, osteoporosis, and rheumatism.

By unloading the spinal column vertebrae of the mechanical forces of the upper body, head and arms, orthotic appliances such as belts, girdles, corsets and braces aid in preventing spinal injury and are used during therapy to support the spinal column. Such orthotic appliances unload the spine, immobilize the spine, or achieve both.

Conventional orthotic appliances unload the spinal column by either increasing intra-abdominal pressure (IAP) or by introducing a rigid outer support frame structure. Increased intra-abdominal pressure (IAP) is achieved with the contraction of a person's diaphragm, abdominal muscles, trunk muscles, and by the person holding his breath (glottis being closed). The increased IAP partially unloads the spinal column by countering the axial compression of the upper torso. Increased IAP may be accompanied by stiffening of the trunk muscles, thereby reducing the possibility of tissue strain.

Flexible spinal orthotic appliances which wrap around the wearer's trunk are employed to compress the abdomen. Weight lifters, warehousemen and others lifting heavy objects typically wear orthotic belts which compress their abdomen.

Other examples of flexible spinal orthotic devices are shown in U.S. Pat. No. 2,250,267 to Lins and U.S. Pat. No. 4,572,167 to Brunswick. The '267 patent discloses a flexible spinal orthotic back support appliance. In particular, the device consists of a pillow case having a resilient band and a pillow or cushion which covers a substantial portion of the wearer's back. The cushion is housed inside the pillow case.

U.S. Pat. No. 4,572,167 to Brunswick is directed to a belt-like device having support panels which mold around the contours of the wearer's body. The belt is held in place by an adjustable strap.

The effectiveness of flexible spinal orthotics appliances are limited to short durations when the wearer is holding his breath. Weight lifters, warehousemen and others lifting heavy objects benefit from the spinal unloading contribution of such appliances.

Flexible spinal orthotic appliances, however, are not effective when the wearer is actively breathing (i.e., walking, jogging) and not holding his breath. In addition, the continuous use of such orthotic support may weaken the trunk muscles which are essential in the support of the spinal column. Hence, flexible spinal orthotic appliances may actually have a deleterious effect contributing to weakening of the spinal support muscles.

Rigid spinal orthotic appliances typically use metal rods to unload pressure from the spinal column by transferring the compressive loads of the wearer's upper trunk, head and arms to the wearer's pelvis.

U.S. Pat. No. 1,722,205 to Freund and U.S. Pat. No. 3,029,810 to Martin are examples of such rigid orthotic appliances. The '205 patent shows a back support device having two long, rigid, threaded, vertically arranged screws and an arcuate arm pit rest at the end of each screw. The screws permit the height of arcuate rests to be adjusted to fit the wearer's body. The screws are held in place around the wearer's body via adjustable straps which wrap around the waist and chest. The load from the wearer's spine is transferred to the two screws.

The '810 is also directed to a back brace which has vertically aligned, adjustable metal rods which fit under the wearer's arm pit to unload compressive forces on the spine to the rods. The metal rods are also held in place by straps which wrap around the waist and chest.

Although the rigid appliances are effective in unloading the spinal column of compressive loads, they restrict the normal motions of the spine. In addition, their use is limited to therapeutic immobilization of the spine following injury or surgery and are not practical for use while exercising.

While spinal appliances may be necessary in order to achieve objectives in the treatment of spinal disorders, the use of appliances may create additional problems. Aside from the inconveniences and relative confinement imposed by the braces, another disadvantage is that the spinal orthoses impair the wearer's gait and energy expenditure.

SUMMARY OF THE INVENTION

The invention is directed to an orthotic belt having a waistband which wraps around a wearer's waist and a pair of hand grips located in the rear of the waistband. In use, the wearer places his hands in the grips and forces the belt downward onto the pelvis thereby unloading the spinal column. The waistband may further include a back support section which supports the wearer's back.

The hand grip may be a strap or a pocket which receives the wearer's hand such that the palm of the wearer's hand is flush with the wearer's back. Alternatively, the hand grips may be a handle or a peg which extends out substantially perpendicular to the waistband. The wearer grips onto the hand grip and pushes downward.

It is therefore an object of the present invention to provide a device that unloads the spinal column of the compressive loads from the upper trunk, head and arms of an individual while providing a flexible device which permits the wearer to walk, jog, or engage in other physical activities.

A further object of the invention is to provide a therapeutic aid for an individual with back injury due to surgery, disc herniation, osteoporosis, rheumatory arthritis, or spinal nerve root compression.

Another object of the invention is to provide a preventative appliance for use by those prone to back injury due to aging and jogging.

A further object of the invention is to provide a postural support appliance for those engaged in physical activity which requires postural alignment and control such as joggers, walkers, back packers, and exercise machine (e.g., stairmaster, stationary bicycles, treadmills) users.

These, and further objects and advantages of the present invention will be made clear or will become apparent during the course of the following description of the preferred embodiment of the present invention.

BRIEF DESCRIPTION OF THE DRAWINGS

In the accompanying drawings:

FIG. 1 is a perspective view of a pelvic belt, having hand grips of the present invention;

FIG. 2 shows a front elevational view of the pelvic belt of FIG. 1 illustrating a wearer's hands in the hand grips;

FIG. 3 is similar to FIG. 2 but shows a rear elevational view of the pelvic belt; and FIG. 4 is similar to FIG. 2 but shows a lateral view of the pelvic belt.

DETAILED DESCRIPTION OF THE PREFERRED EMBODIMENT

Referring to FIG. 1, a pelvic 10 belt with hand grips is illustrated. The pelvic belt 10 includes a waistband A and a pair of hand grips B attached to the rear of the waistband A. In particular, the pair of hand grips B are attached to the rear of the waistband A in a location corresponding to where the waistband would rest upon the wearer's pelvic bones above the wearer's buttocks. In the preferred embodiment, the hand grips B are mounted on the waistband A at a slight angle.

As illustrated, the hand grip B includes a strap that is open on its top and bottom sides and attaches to the waistband A on its other two sides. However, the hand grip B may be a pocket (i.e., open on its top side and closed on its other three sides).

The strap B may be secured onto the waistband A via rivets 6. The strap B has a plurality of vertically arranged rivets which fit into corresponding rivet holes 3 in the waistband A.

The belt 10 may also have several rows of alternative rivet holes 3 to permit the location of the hand grip 5 to be changed to adapt to wearer's having different size pelvic bone structure. While hand grips B of the preferred embodiment are adjustable attachments, they may be permanently affixed to the waistband A. Hence, the hand grips B may be attached by stitching, rivets, buckles, Velcro, laces or adhesives.

The hand grips B may be made of a flexible, rigid, elastic or plastic material such as leather, plastic, wood, metal or other synthetic polymer material.

In the preferred embodiment the waistband A also includes a back support section 2, and a pair of belt straps 1a, 1b on either side of the back support section 2. The back support section 2 is wider than the waistband A. As illustrated, the back support section 2 is curved-shaped. The back support section 2 has a width which may be varied.

The waistband A may be made of a flexible, rigid, elastic, plastic material as leather, rubber, plastic, or other synthetic polymer material.

The belt straps 1a, 1b may be joined together by using a belt buckle 4, as illustrated, or using rivets, Velcro, stitching, or laces.

Referring to FIGS. 2-4, when the pelvic belt 10 is wrapped around the wearer, the waistband A encircles the wearer's waist above and upon the pelvic and sacral bone protrusions. The width, thickness, and texture of the waistband A may vary. Depending upon the width, thickness and texture, the waistband A may also provide support for proximal body members, such as the buttocks, pelvis, back and abdomen.

Unlike the conventional flexible orthotic support appliances (which are designed to be affixed tightly around the wearer's abdomen to increase intra-abdominal pressure), the pelvic belt 10 is not designed to be worn to cause IAP. The belt 10 is secured with a tautness about equal to the tautness that one normally wears a conventional belt.

The manner of using the pelvic belt 10 also differs from the manner in which conventional spinal unloading orthotic appliances are used. In using the pelvic belt with hand grips 10, the wearer applies downward pressure, using his hands, on the hand grips B thereby resting his arms on the hand grips B. By applying pressure to the hand grips B, the belt 10 is forced downward onto the wearer's pelvis. As the wearer presses downward, the compressive loads on his spinal column are transferred from his spine onto the pelvic bones. The harder the wearer pushes downward, the greater the pressure exerted onto the pelvic belt 10 and greater the amount of pressure that is relieved from the wearer's spinal column.

The pelvic belt 10 may be worn while walking, hiking, jogging and exercise to relieve pressure off the user's spinal column. Unlike the conventional rigid orthotic appliances the pelvic belt 10 is relatively unobtrusive and does not significantly interfere with the user's bodily movement.

Having thus described the invention, it is recognized that those skilled in the art may make various modifications or additions to the preferred embodiment chosen to illustrate the invention without departing from the spirit and scope of the present contribution to the art. Accordingly, it is to be understood that the protection sought and to be afforded hereby should be deemed to extend to the subject matter claimed and all equivalents thereof within the scope of the invention.

What is claimed is:

1. A method of using an orthotic belt to reduce compressive forces on a wearer's spinal column, comprising the steps of:

providing an orthotic belt having a waistband means and a pair of gripping means;

positioning the waistband means around the wearer such that the gripping means are positioned at about the iliac crest region to allow force transfer onto the iliac crest region of the wearer's pelvis;

gripping the pair of gripping means with the wearer's hands; and applying sufficient downward force on the gripped gripping means such that a portion of the compressive forces present on the wearer's spinal column is transferred onto the wearer's pelvis.

2. The method of claim 1 wherein the step of applying downward force is performed by pushing downward on the gripped gripping means;

3. The method of claim 1 wherein the step of applying downward force is performed by pulling downward on the gripped gripping means.

4. The method of claim 1 wherein the gripping means includes a strap for receiving a hand.

5. The method of claim 1 wherein the gripping means includes a pocket.

6. The method of claim 1 wherein the gripping means includes a handle.

7. The method of claim 1, wherein the step of positioning includes the step of wrapping the waistband means around the wearer's waist.

8. The method of claim 1 further including the step of:
securing the positioned waistband means around the wearer's waist such that the gripping means are located to allow the force transfer upon the iliac crest region of the wearer's pelvis.

9. A method of using an orthotic belt to reduce compressive forces on a wearer's vertebral column, comprising the steps of:
providing an orthotic belt having a waistband means for wrapping around the wearer's waist and a pair of gripping means;
wrapping the waistband means around the wearer's waist;
positioning the gripping means at about the posterior iliac crest region of the wearer's pelvis; and
applying a downward force on the gripping means using the wearer's hands such that at least a portion of the compressive forces on the wearer's vertebral column is transferred onto the wearer's pelvis.

10. The method of claim 9 wherein the step of applying a downward force is performed by pushing downward on the gripping means.

11. The method of claim 9 wherein the step of applying a downward force is performed by pulling downward on the gripping means.

12. The method of claim 9 wherein the gripping means includes a strap for receiving a hand.

13. The method of claim 9 wherein the gripping means includes a pocket.

14. The method of claim 9 wherein the gripping means includes a handle.

15. The method of claim 9 wherein the gripping means includes a force transferring means for manual engagement with the wearer's hand.

16. The method of claim 9 further including the step of:
securing the waistband means around the wearer's waist.

17. A method of using an orthotic belt to reduce compressive forces on a wearer's vertebral column, comprising the steps of:
providing an orthotic belt having a waistband means and a manually engageable force transferring means for releasable gripping;
positioning the manually engagable force transferring means at about the posterior iliac crest region of the wearer's pelvis; and
applying sufficient downward pressure on the manually engagable force transferring means using the wearer's hands such that at least a portion of the compressive forces on the wearer's vertebral column are transferred onto the wearer's pelvis.

18. The method of claim 17 wherein the step of applying a sufficient downward pressure is performed by pushing downward on the gripped gripping means.

19. The method of claim 17 wherein the step of applying a sufficient downward pressure is performed by pulling downward on the gripped gripping means.

20. The method of claim 17 wherein the step of positioning the waistband means includes the steps of:
wrapping the waistband means around the wearer's waist; and
securing the waistband means around the wearer's waist.

21. The method of claim 17 wherein the manually engagable force transferring means includes a strap for receiving a hand.

22. The method of claim 17 wherein the manually engagable force transferring means includes a pocket.

23. The method of claim 17 wherein the manually engagable force transferring means includes a handle.

24. A method for using an orthotic belt comprising the steps of:
providing an orthotic belt having a waistband and a pair of manually engagable force transferring means;
positioning the waistband around a wearer's waist such that the force transferring means are located at about the iliac crest region of the wearer's pelvis;
engaging each of the force transferring means with a respective one of the wearer's hands; and
applying a sufficient downward force on each of the engaged force transferring means to transfer a portion of the compressive forces on the wearer's spinal column onto the wearer's pelvis.

25. The method of claim 24 wherein the step of applying a sufficient downward force is performed by pushing downward on the engaged force transferring means.

26. The method of claim 24 wherein the step of applying a sufficient downward force is performed by pulling downward on the engaged force transferring means.

27. The method of claim 24 wherein the step of positioning the waistband means includes the steps of:
wrapping the waistband means around the wearer's waist; and
securing the waistband means around the wearer's waist.

28. The method of claim 24 wherein the manually engagable force transferring means includes a strap for receiving a hand.

29. The method of claim 24 wherein the manually engagable force transferring means includes a pocket.

30. The method of claim 24 wherein the manually engagable force transferring means includes a handle.

* * * * *